(12) United States Patent
Vignon et al.

(10) Patent No.: US 11,391,828 B2
(45) Date of Patent: Jul. 19, 2022

(54) METHODS AND SYSTEMS FOR FILTERING ULTRASOUND IMAGE CLUTTER

(71) Applicant: KONINKLIJKE PHILIPS N.V., Eindhoven (NL)

(72) Inventors: Francois Guy Gerard Marie Vignon, Andover, MA (US); Jun Seob Shin, Medford, MA (US); Sheng-Wen Huang, Ossining, NY (US); Jean-Luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 140 days.

(21) Appl. No.: 16/462,276

(22) PCT Filed: Nov. 27, 2017

(86) PCT No.: PCT/EP2017/080551
§ 371 (c)(1),
(2) Date: May 20, 2019

(87) PCT Pub. No.: WO2018/099867
PCT Pub. Date: Jun. 7, 2018

(65) Prior Publication Data
US 2019/0369220 A1 Dec. 5, 2019

Related U.S. Application Data

(60) Provisional application No. 62/427,204, filed on Nov. 29, 2016.

(30) Foreign Application Priority Data

Dec. 15, 2016 (EP) .................................. 16204209

(51) Int. Cl.
*G01S 7/52* (2006.01)
*A61B 8/08* (2006.01)
*A61B 8/00* (2006.01)

(52) U.S. Cl.
CPC ........ *G01S 7/52077* (2013.01); *A61B 8/4488* (2013.01); *A61B 8/5269* (2013.01); *A61B 8/54* (2013.01)

(58) Field of Classification Search
CPC ............ G01S 7/52077; G01S 15/8977; A61B 8/4488; A61B 8/5269; A61B 8/54
See application file for complete search history.

(56) References Cited

U.S. PATENT DOCUMENTS 5,997,479 A 12/1999 Savord
6,013,032 A 1/2000 Savord
(Continued)

OTHER PUBLICATIONS

Demene et al "Spatiotemporal Clutter Filtering of Ultrafast Ultrasound Data Highly Increases Doppler and fultrasound Sensitivity" IEEE Trans Med Imaging. Nov. 2015;34(11):2271-85. doi: 10.1109/TML.2015.2428634. Epub Apr. 30, 2015.
(Continued)

*Primary Examiner* — Joseph M Santos Rodriguez
*Assistant Examiner* — Kaitlyn E Sebastian (57) ABSTRACT

A method is provided for filtering ultrasound image clutter. In the first stage of the method a data matrix is captured, wherein the data matrix contains information relating to the image, and singular value decomposition (SVD) is performed on the data matrix or a matrix derived from the data matrix. A spatial singular vector is then obtained from the SVD of the data matrix and a mean spatial frequency is estimated from them. A filtered data matrix is constructed based on the estimated mean spatial frequency and the SVD of the data matrix and a filtered image is constructed based on the filtered data matrix.

20 Claims, 3 Drawing Sheets

(56) References Cited

U.S. PATENT DOCUMENTS

| | | |
|---|---|---|
| 6,283,919 B1 | 9/2001 | Roundhill et al. |
| 6,443,896 B1 | 9/2002 | Detmer |
| 6,458,083 B1 | 10/2002 | Jago et al. |
| 6,530,885 B1 | 3/2003 | Entrekin et al. |
| 6,623,432 B2 | 9/2003 | Powers et al. |
| 8,684,934 B2 | 4/2014 | Kim |
| 9,002,080 B2 | 4/2015 | Mauldin et al. |
| 9,232,931 B2 | 1/2016 | Kim |
| 2006/0058974 A1* | 3/2006 | Lasiuk ............... G01B 15/025 702/97 |
| 2009/0079299 A1* | 3/2009 | Bradley ............. G01S 15/8927 310/322 |
| 2011/0118606 A1* | 5/2011 | Kim ................... G01S 15/8981 600/453 |
| 2012/0163691 A1* | 6/2012 | Walker ..................... A61B 8/00 382/131 |
| 2012/0216617 A1* | 8/2012 | Hoctor ................ G01N 29/262 73/602 |
| 2013/0094729 A1* | 4/2013 | Mauldin, Jr. ......... A61B 8/5207 382/128 |
| 2020/0138401 A1* | 5/2020 | Haugaard ........... G01S 15/8984 |

OTHER PUBLICATIONS

Mauldin et al "The Singular Value Filter: A General Filter Design Strategy for PCA-Based Signal Separation in Medical Ultrasound Imaging" IEEE Transactions on Medical Imaging, vol. 30, No. 11 Nov. 2011 p. 1951-1964.

Bjaerum et al "Optimal Adapive Clutter Filtering in Color Flow Imaging" 1997 IEEE Ultrasound Symposium p. 1223-1226.

A. Yu and L. Lovstakken "Eigen-Based Clutter Filter Design for Ultrasound Color Flow Imaging: A Review"; IEEE Trans. Ultr. Ferr. Freq. Contr. 57(5), May 2010, pp. 1096-1111.

Yu, ACH; Cobbold, RSC; "Single-ensemble-based eigen-processing methods for color flow imaging—Part I. The Hankel-SVD filter" IEEE Transactions On Ultrasonics, Ferroelectrics, And Frequency Control, 2008, 55(3), p. 559-572.

Yu et al "A New Eigen-Based Clutter Filter Using the Hankel SVD Approach" Ultrasonics Symposium 2006, IEEE Oct. 1, 2006, p. 1079-1082.

Shin et al "Spatial Prediction Filtring of Acoustic Clutter and Random Noise in Medical Ultrasound Imaging" IEEE Transactions on Medical Imaging vol. 36, No. 2 Sep. 16, 2016 p. 396-406.

International Search Report dated Feb. 27, 2018.

* cited by examiner

METHODS AND SYSTEMS FOR FILTERING ULTRASOUND IMAGE CLUTTER

FIELD OF THE INVENTION

This invention relates to the field of ultrasound image processing, and more specifically to the field of eigenvector-based clutter filtering.

BACKGROUND OF THE INVENTION

Ultrasound imaging is increasingly being employed in a variety of different applications. It is important that the image produced by the ultrasound system is as clear and accurate as possible so as to give the user a realistic interpretation of the subject being scanned. This is especially the case when the subject in question is a patient undergoing a medical ultrasound scan. In this situation, the ability of a doctor to make an accurate diagnosis is dependent on the quality of the image produced by the ultrasound system.

Recent advances in ultrasound technology have greatly improved the image quality and reliability, however, off-axis clutter remains a significant cause of image degradation in ultrasound. Off-axis clutter is a noise artefact that appears as diffuse echoes overlying the signals of interest in the ultrasound image. This clutter often obscures the region of interest making anatomical measurements, key to the diagnosis, difficult to perform accurately.

Several adaptive techniques for off-axis clutter reduction have been developed, including; aberration correction, coherence factor weighting, and other adaptive beamforming techniques based on the covariance of the per-channel data such as minimum-variance beamforming. Beamforming techniques are based in the spatial domain of signals measured along a channel in line with the ultrasonic transducer aperture. In this case, the distinguishing feature of the off-axis clutter signals is their high spatial frequency and the signals are often filtered using a low-pass filter.

Alternative eigenvector-based techniques have been employed in the field of Doppler filtering, which relate to the slow-time behaviour of the clutter signals. A covariance matrix is formed from the ultrasound data, the eigenvectors of which correspond to the different motion modes of the target tissue in slow-time. By analysing the frequency content of the temporal eigenvectors and attenuating those with low temporal frequencies, corresponding to slow-moving clutter, off-axis clutter may be filtered in an adaptive manner. In other words, for Doppler based techniques, the distinguishing feature of the off-axis clutter signals is their low temporal frequency and the signals are often filtered using a high-pass filter.

Yu, Alfred C. H. et al "A New Eigen-Based Clutter Filter Using the Hankel SVD Approach" discloses a method for performing Eigen-based filtering in colour flow data processing.

SUMMARY OF THE INVENTION

The invention is defined by the claims.

According to examples in accordance with an aspect of the invention, there is provided a method for filtering ultrasound image clutter, comprising:

capturing a data matrix, the matrix containing information relating to an image, wherein elements of each row or column of the matrix correspond to individual measurements recorded for each of a plurality of ultrasound measurement channels;

performing singular value decomposition, SVD, on the data matrix or a matrix derived from the data matrix;

obtaining a spatial singular vector from the SVD of the data matrix;

estimating a mean spatial frequency from the spatial singular vector;

constructing a filtered data matrix based on the estimated mean spatial frequency and the SVD of the data matrix; and constructing a filtered image based on the filtered data matrix.

This method performs eigenvector filtering on an ultrasound image in order to reduce the amount of off-axis clutter in the final image. A medical ultrasound scanner commonly includes an ultrasound transducer capable of emitting and receiving ultrasonic signals. These signals are often received in the form of complex envelope signals, also known as wave packets. By capturing these signals in matrix form, it is possible to analyse and manipulate the data in a number of ways.

Singular value decomposition (SVD) of a matrix is a form of matrix factorization that results in a single matrix being split into three constituent matrices. For example, in the case of the data matrix $\overline{Y}$, singular value decomposition would result in $\overline{Y} = \overline{U}\overline{S}\overline{V}^H$, wherein $\overline{U}$ is a square unitary matrix, $\overline{S}$ is a diagonal matrix and $\overline{V}^H$ is a square unitary matrix and the conjugate transpose of the square unitary matrix $\overline{V}$. The diagonal entries of matrix $\overline{S}$ are known as the singular values of $\overline{Y}$ and the columns of matrices $\overline{U}$ and $\overline{V}$ are known as the left-singular vectors, $\overline{U}_j$, and right-singular vectors, $\overline{V}_j$, of data matrix $\overline{Y}$ respectively. In this way, it is possible to isolate and analyse the components of the complex signal data stored in the data matrix.

By obtaining the right-singular vector from the SVD of the data matrix, which corresponds to a spatial singular vector, and using it to estimate a mean spatial frequency for a signal, it is possible to identify signals that would contribute to the off-axis clutter in the final image. Through eliminating, or attenuating, the signals containing off-axis clutter, it is possible to construct a filtered data matrix, $\overline{Y}_{hat}$, with the remaining filtered signals. The signals within the filtered data matrix can then be used to calculate a filtered pixel value, which may then be used to construct a clutter-filtered image.

In some arrangements the data matrix comprises:

N columns, wherein N corresponds to a number of ultrasound measurement channels; and M rows, wherein M corresponds to a number of independent measurements recorded for each channel.

In this design, the data matrix $\overline{Y}$ is an M×N rectangular matrix. Correspondingly, $\overline{U}$ is an M×M square unitary matrix, $\overline{S}$ is an M×N rectangular diagonal matrix and $\overline{V}^H$ is an N×N square unitary matrix.

In further arrangements, the recording of the M independent measurements is performed by:

capturing data from each measurement channel at M points in time during a desired time interval; or insonifying the measurement area with M overlapping ultrasonic transmits; or dividing the physical receive aperture into M overlapping subarrays of size N.

In this way, multiple independent measurements of the same position in the image are used to reduce the risk of including a random error in the final image.

In some designs, the method further comprises forming a covariance matrix based on the data matrix, wherein the singular value decomposition is performed on the covariance matrix.

The covariance matrix $\overline{R}$ takes the form of $\overline{R}=\overline{Y}^H\overline{Y}$, wherein $\overline{Y}$ is the captured data matrix and $\overline{Y}^H$ is the conjugate transpose of $\overline{Y}$. In some instances it may be more computationally efficient to perform the SVD on the covariance matrix rather than the data matrix.

The data and covariance matrices can alternatively be built in the space-frequency domain. In this case, short-time fast-time Fourier transforms of the data are performed and a data or covariance matrix is formed at each frequency by either subarray averaging or combined transmit events, or both.

In some embodiments, the obtained spatial singular vector comprises a spatial eigenvector of the data matrix. The complex signals captured in the data matrix contain spatial information relating to the ultrasound image, such as a lateral dimension, along the transducer array, and the depth of the received signal. Upon performing the singular value decomposition on the data matrix, the spatial eigenvectors relating to each measurement point are placed into the columns of matrix $\overline{V}$, which correspond to the right-singular vectors of the data matrix.

In one arrangement, the mean spatial frequency of the spatial eigenvector is estimated using the autocorrelation technique. The autocorrelation technique is a method for estimating the mean frequency in a complex signal. In some cases, the estimation for the mean spatial frequency is calculated based on the autocorrelation of the data, with lag one, evaluated over the N samples.

In one embodiment, the step of constructing the filtered data matrix comprises:
  determining a weighting based on the estimated mean spatial frequency;
  applying the weighting to the associated spatial singular vector; and
  using the weighted spatial singular vector in the construction of the filtered data matrix.

In a further embodiment, the weighting is equal to a maximum of one, for a spatial singular vector with an estimated mean spatial frequency of zero, and decreases to a minimum of zero as the estimated mean spatial frequency increases.

Spatial singular vectors with a spatial frequency of zero correspond to on-axis signals, meaning that they have been measured in the correct location, whereas spatial singular vectors with a high spatial frequency correspond to signals that contain large amounts of off-axis clutter. By applying a weighting to the spatial singular vector, based on the associated mean spatial frequency, it is possible to attenuate the off-axis signals and reduce or eliminate their contributions to the final image, thereby reducing the off-axis clutter in the final image.

In one design, the weighting is determined using Gaussian weighting that includes a reference spatial frequency and in further embodiments the reference spatial frequency corresponds to the transmit beam width, wherein the transmit beam width is the angular width of the transmit beam.

In some arrangements, the method comprises discarding a spatial singular vector with a mean spatial frequency above a predetermined value or with a very low corresponding eigenvalue. By limiting the number of spatial singular vectors by eliminating those with a significantly large clutter component or low eigenvalue, the image quality can be improved and the computational cost of the method reduced, for example, by computing only the first few eigenvectors, which explain most of the signal.

In some designs, the constructing of the filtered data matrix is further based on the amplitude of the received signal. For example, if the image clutter is expected to be of lower amplitude than the signal, magnitude-based filtering can be used to improve image quality. In other words, lower energy spatial singular vectors are further attenuated by the filtering process.

Examples in accordance with a further aspect of the invention provide a controller for filtering image clutter in an ultrasound system, wherein the controller is adapted to:
  capture a data matrix, the data matrix containing information relating to an image, wherein elements of each row or column of the matrix correspond to individual measurements recorded for each of a plurality of ultrasound measurement channels;
  perform singular value decomposition (SVD) on the data matrix or a matrix derived from the data matrix;
  obtain a spatial singular vector from the SVD of the data matrix;
  estimate a mean spatial frequency from the spatial singular vector;
  construct a filtered data matrix based on the estimated mean spatial frequency and the SVD of the data matrix; and
  construct a filtered image based on the filtered data matrix.

According to examples in accordance with another aspect of the invention, there is provided an ultrasound system comprising:
  an ultrasonic transducer array, wherein the ultrasonic transducer array is capable of emitting and receiving ultrasonic signals;
  a signal processor for compiling the received ultrasonic signals into an ultrasound image;
  a system for generating a data matrix from the ultrasound image;
  a controller, wherein the controller is adapted to:
    capture a data matrix, the data matrix containing information relating to an image, wherein elements of each row or column of the matrix correspond to individual measurements recorded for each of a plurality of ultrasound measurement channels;
    perform singular value decomposition (SVD) on the data matrix or a matrix derived from the data matrix;
    obtain a spatial singular vector from the SVD of the data matrix;
    estimate a mean spatial frequency from the spatial singular vector;
    construct a filtered data matrix based on the estimated mean spatial frequency and the SVD of the data matrix; and
    construct a filtered image based on the filtered data matrix; and
  an image output device for outputting the filtered image.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a method for filtering ultrasound image clutter. In the first stage of the method a data matrix is captured, wherein the data matrix contains information relating to the image, and singular value decomposition (SVD) is performed on the data matrix or a matrix derived from the data matrix. A spatial singular vector is then obtained from the SVD of the data matrix and a mean spatial frequency is estimated from them. A filtered data matrix is constructed based on the estimated mean spatial frequency and the SVD of the data matrix and a filtered image is constructed based on the filtered data matrix.

The general operation of an ultrasound diagnostic imaging system will first be described, with reference to FIG. 1, and with emphasis on the signal processing function of the system since this disclosure relates to the processing and filtering of the signals measured by the transducer array.

The ultrasound diagnostic imaging system 5 comprises an array transducer probe 10 which has a transducer array 100 for transmitting ultrasound waves and receiving echo information. The transducer array 100 may be a capacitive micromachined ultrasonic transducer (CMUT) array, or may alternatively comprise piezoelectric transducers formed of materials such as lead zirconate titanate (PZT) or polyvinylidene fluoride (PVDF). The transducer array 100 is a two-dimensional array of transducers 110 capable of scanning in a 2D plane or in three dimensions for 3D imaging.

The transducer array 100 is coupled to a microbeamformer 12 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 12 is coupled by the probe cable to a transmit/receive (T/R) switch 16 which switches between transmission and reception and protects a main receive beamformer 20 from high energy transmit signals when a microbeamformer is not used and the transducer array 100 is operated directly by the main system beamformer. The transmission of ultrasound beams from the array transducer probe 10 is directed by a transducer controller 18 coupled to the microbeamformer by the T/R switch 16 and a main transmission beamformer (not shown), which receives input from the user's operation of the user control panel or user interface 38.

One of the functions controlled by the transducer controller 18 is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to the main receive beamformer 20 where the partially beamformed signals from individual patches of transducers are combined into a fully beamformed signal. For example, the main receive beamformer 20 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed taking into account the characteristics of the transmission beamformer. In FIG. 1 only the receiver beamformers 12, 20 are shown, for simplicity. In the complete system, there will also be a transmission chain with a transmission microbeamformer, and a main transmission beamformer.

The function of the microbeamformer 12 is to provide an initial combination of signals in order to decrease the number of analog signal paths. This is typically performed in the analog domain.

The final beamforming is done in the main receive beamformer 20 and is typically after digitization.

The transmission and reception channels use the same transducer array 100 which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow as well as structural measurements such as the sizes of organs and gestational age. The quantification processor may receive input from the user interface 38, such as the point in the anatomy of an image where a measurement is to be made. Output data from the quantification processor is coupled to a graphics processor 36 for the reproduction of measurement graphics and values with the image on the display 40, and for audio output from the image display 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transducer controller 18 to control the generation of ultrasound signals from the transducer array 100 and hence the images produced by the transducer array 100 and the ultrasound system. The transmit control function of the transducer controller 18 is only one of the functions performed. The transducer controller 18 also takes account of the mode of operation (given by the user) and the corresponding required transmitter configuration and bandpass configuration in the receiver analog to digital converter. The transducer controller 18 can be a state machine with fixed states.

The user interface 38 is also coupled to the multi-planar reformatter 44 for selection and control of the planes of multiple multi-planar reformatted (MPR) images which may be used to perform quantified measures in the image field of the MPR images.

Figure 1:
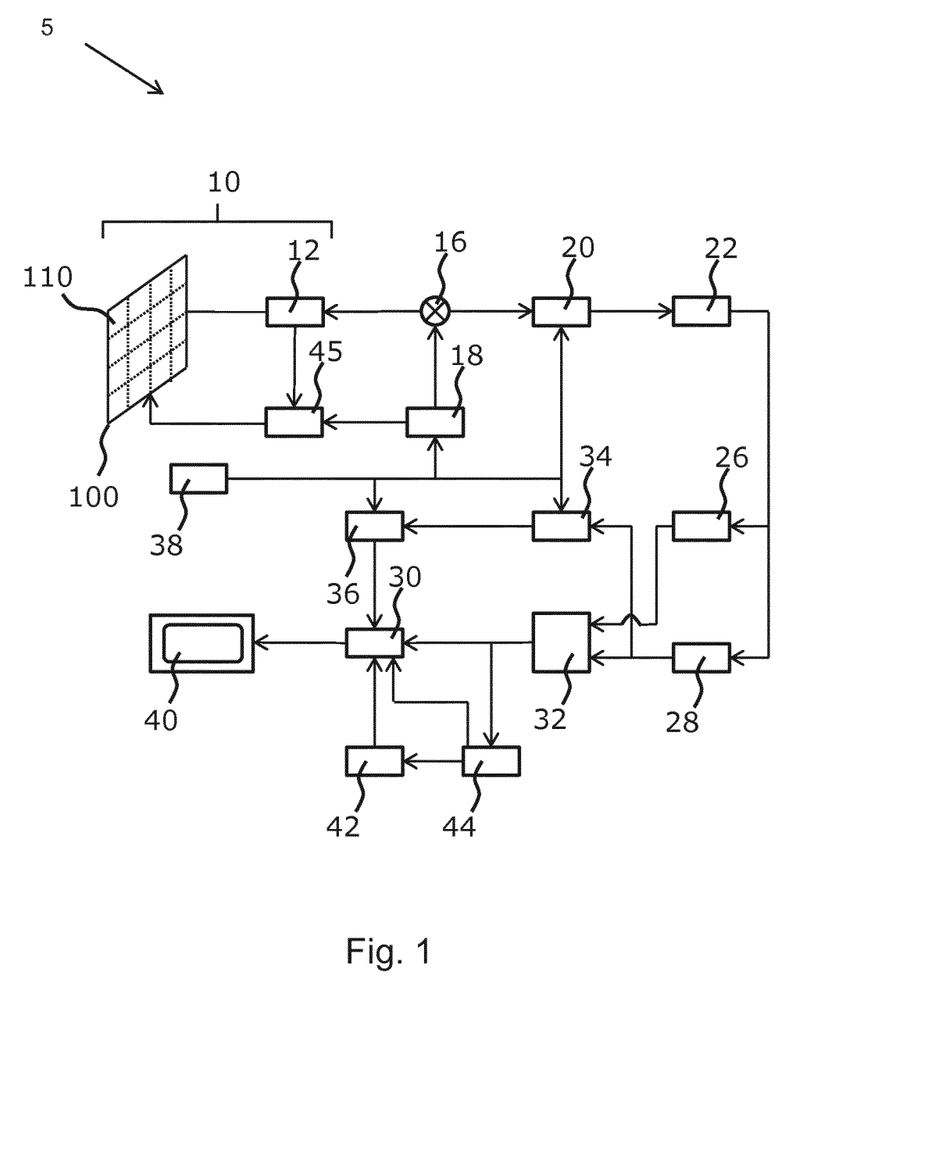
FIG. 1 shows an ultrasound diagnostic imaging system to explain the general operation.
Figure 2:
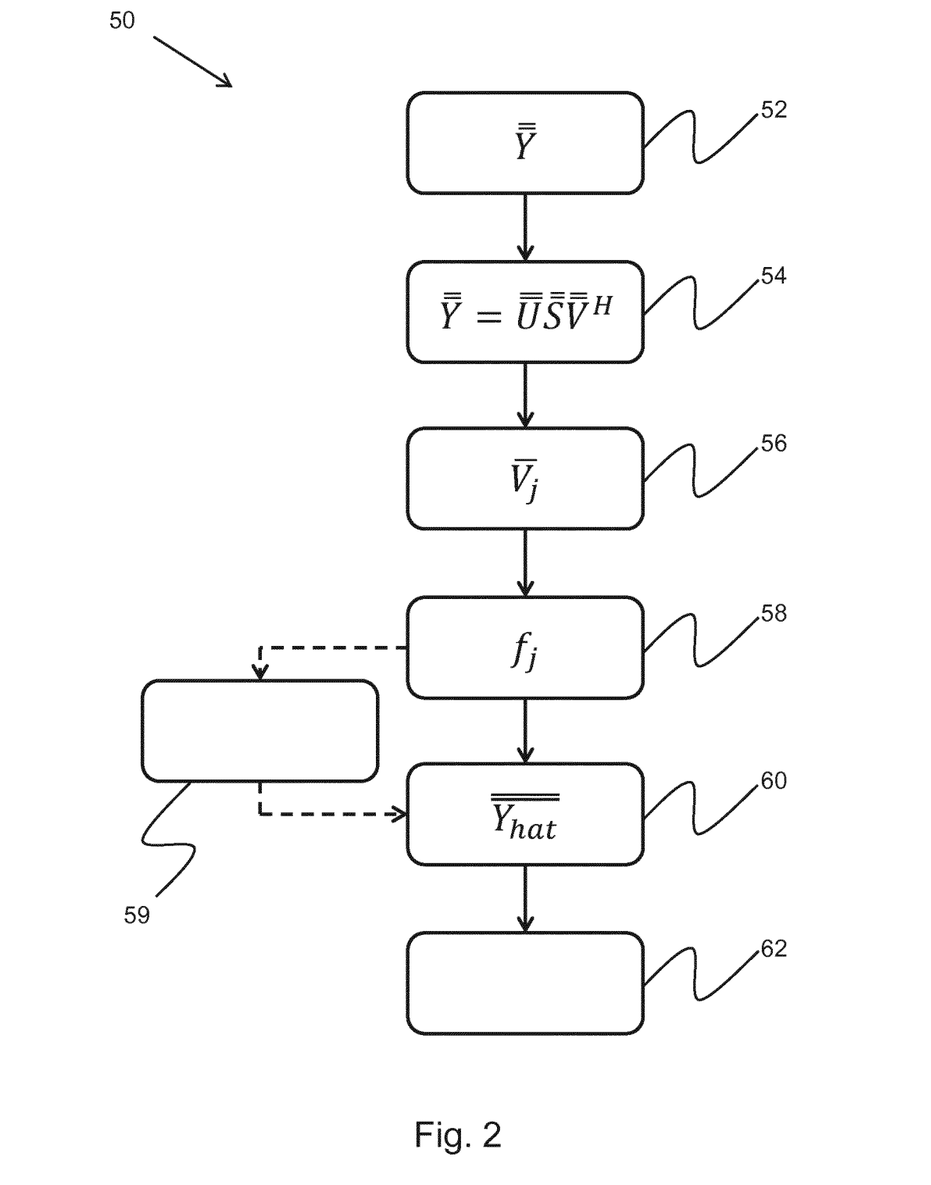
FIG. 2 shows a method of the invention.

FIG. 2 shows a method 50 of the invention that may for example be implemented by signal processor 22, shown in FIG. 1, or by a separate dedicated controller.

In step 52, a data matrix $\overline{Y}$ is captured from a set of ultrasound signals and contains information relating to an ultrasound image. The data matrix $\overline{Y}$ may take the form of an M×N rectangular matrix, wherein the N columns correspond to N measurement points in the image and the M rows correspond to M independent measurements taken at each measurement point.

It is possible to perform M independent measurements of a point in a number of ways. In the simplest example, data is captured from the N measurement channels at M points in time during a desired time period. In a further example, the measurement area is insonified with M overlapping ultrasonic transmits. For this example, the ultrasonic system uses an ultrasonic transducer array that produces waves that overlap the point of interest. The echoes caused by these waves are then detected and measured by the N transducer elements within the ultrasonic transducer array. By insonifying the target region with M overlapping waves, the N transducer elements will be able to perform M independent measurements on the returned echoes. In another example, the physical receive aperture, where the ultrasonic transducer array is located, may be divided into M overlapping subarrays of size N. In this way, the overlapping subarrays will be able to record M independent results through the process of subarray averaging. Subarray averaging is performed on a subarray, of size N, by dividing the subarray into overlapping sub-apertures of size L, where L is less than N. The data from these sub-apertures is then used as the M independent measurements, where M=N−L+1. In other words, each overlapping sub-aperture of size L constitutes one of M observations. In this way, an M×N data matrix can be formed.

It is possible to use these examples in combination with each other to gather the desired number of independent measurements.

In step 54, a singular value decomposition (SVD) is performed on the data matrix $\overline{Y}$. Singular value decomposition is a form of matrix factorisation, resulting in the following equation.

$$\overline{Y} = \overline{U}\overline{S}\overline{V}^H$$

Where $\overline{U}$ is an M×M square unitary matrix, $\overline{S}$ is an M×N rectangular diagonal matrix and $\overline{V}^H$ is an N×N square unitary matrix and is the conjugate transpose of the N×N square unitary matrix $\overline{V}$, for the case where $\overline{Y}$ is an M×N rectangular matrix. The diagonal elements of matrix $\overline{S}$ are the singular values of the data matrix.

By factorising the data matrix containing the complex measurement signals from the ultrasonic transducer, it is possible to isolate and analyse the components of the signals in a simple form. For example, when the data matrix contains ultrasound signals relating to an image, performing the singular value decomposition on the data matrix will separate the temporal and spatial information into separate matrices. In this way, the contents of these simple matrices may be analysed and used in a simple and efficient manner.

In step 56, a spatial singular vector, $\overline{V}_j$, is obtained from the SVD of the data matrix. The columns of matrices $\overline{U}$ and $\overline{V}$ are the left-singular vectors, $\overline{U}_j$, and right-singular vectors, $\overline{V}_j$, of the data matrix respectively. In this case, the right-singular vector corresponds to the spatial singular vector. In some embodiments the right-singular vector, $\overline{V}_j$ wherein j represents the $j^{th}$ column of the matrix $\overline{V}$, comprises a spatial eigenvector of the data matrix. The spatial eigenvectors describe the spatial components of the signals measured by the ultrasonic transducers, such as lateral dimension, along the transducer array, and the depth of the received signal.

In step 58, a mean spatial frequency, $f_j$, is estimated for each spatial singular vector, $\overline{V}_j$. Spatial frequency is a measurement of the periodicity of a structure across a given space. More specifically, it is a measure of how often the sinusoidal components, determined by the Fourier transform, of the structure repeat across a given space. In the spatial domain, off-axis clutter is characterised by a high spatial frequency. By calculating the mean spatial frequency of a spatial singular vector, corresponding to a measurement point, it is possible to identify measurement channels containing a high level of clutter.

In some cases, the mean spatial frequency may be estimated using the auto correlation technique. The autocorrelation technique is a method for estimating the mean frequency in a complex signal using the following formula.

$$f_j = \left(\frac{1}{2\pi}\right)\arg\left(\sum_i^{N-1} \overline{V}_{j,i}\overline{V}_{j,i+1}^*\right)$$

Where $f_j$ is the mean spatial frequency of the $j^{th}$ right-singular vector, $\overline{V}_{j,i}$ is the $i^{th}$ element of the $j^{th}$ right-singular vector and $\overline{V}_{j,i+1}^*$ is the complex conjugate of the $i+1^{th}$ element of the $j^{th}$ right-singular vector.

Some embodiments include a step 59, wherein a spatial singular vector is discarded if the mean spatial frequency of the set is above a predetermined value. At large spatial frequencies, the signal becomes predominantly clutter and the process of filtering the signal will result in negligible useful information for the reconstruction of the image. In some cases, it is possible to predetermine a fixed number of eigenvectors to compute, to stop computing eigenvectors once the associated eigenvalue falls below a predetermined threshold, or to stop computing eigenvectors when the sum of computed eigenvalues exceeds a predetermined threshold. In these ways, the computational cost of performing the clutter filtering may be reduced.

In step 60, a filtered data matrix, $\overline{Y}_{hat}$, is constructed based on the mean spatial frequency estimated in step 58 and the SVD on the data matrix performed in step 54. The filtered data matrix contains the filtered signals from the data matrix captured in step 52 that can be used in the construction of a clutter-filtered image.

In step 62, a filtered image is constructed based on the contents of the filtered data matrix. By summing the values for each measurement channel, held in the columns of the filtered data matrix, it is possible to determine a clutter-filtered pixel value for the associated measurement point.

In some cases, the singular value decomposition, in step 54, is performed on the covariance matrix $\overline{R}$ calculated from the data matrix as, $\overline{R}=\overline{Y}^H\overline{Y}$, where $\overline{Y}^H$ is the conjugate transpose of the data matrix. This course of action would be taken in the situation where it is more computationally cost effective to perform the singular value decomposition on the covariant matrix rather than the data matrix. The covariance matrix can be built at each frequency in the frequency domain by taking the fast-time fast Fourier transform of an M×N observation window, building M measurements, at each frequency, by either subarray averaging or combined transmit events, or both. In this case, the filtered data matrix contains signals in the frequency domain, rather than the spatial domain, and so an inverse fast Fourier transform must be performed to bring the data into the spatial domain prior to reconstructing the image.

Figure 3:
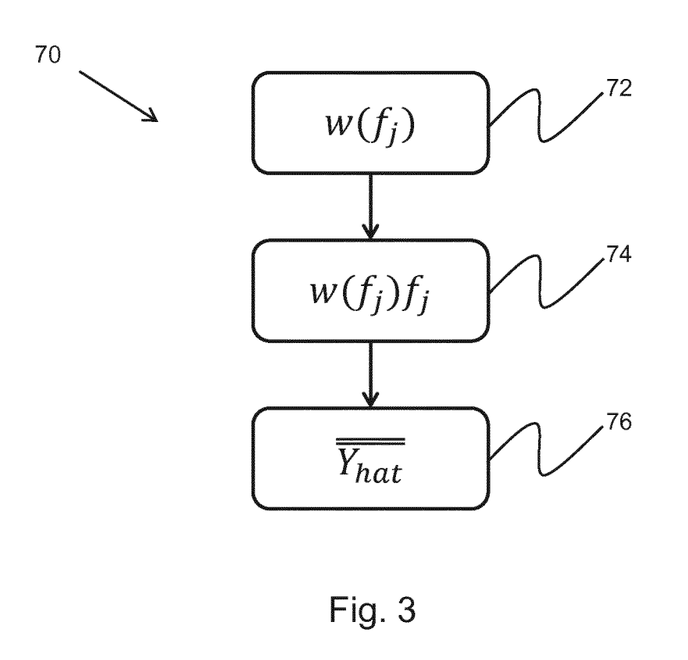
FIG. 3 shows an embodiment of a method for constructing the filtered data matrix.

FIG. 3 shows an embodiment of a method 70 for constructing the filtered data matrix.

In step 72, a weighting is determined based on the mean spatial frequency. A weighting is determined for each spatial singular vector using the mean spatial frequency. In one design, the method used to determine the weighting for a spatial singular vector is Gaussian weighting. The Gaussian weighting is written as, $$w(f_j) = e^{-\frac{f_j^2}{2f_0^2}}$$

wherein $f_j$ is the estimated mean spatial frequency and $f_0$ is known as the reference spatial frequency. In a further embodiment, the reference spatial frequency corresponds to the transmit beam width.

In a further example, the weighting may also be calculated in terms of signal amplitude. If the image clutter is expected to be of lower amplitude than the signal, magnitude-based filtering can be used to improve image quality. In other words, lower energy spatial singular vectors are further attenuated by the filtering process. In addition, it is also possible to determine the weighting based on the slow-time behaviour of the signals. In this case, clutter is characterized by its slow motion when compared with the tissue. Put another way, the temporal characteristics may also be used to calculate the weighting of the spatial singular vectors. In this case, a spatio-temporal covariance matrix is required for each measurement point. Returning to the case of determining the weighting based on the spatial information included in the signal, it is possible to identify clutter signals by the spatial distribution in the eigenvectors, or spatial singular vectors, allowing them to be removed from the final image.

In step 74, the weighting determined in step 72 is applied to the spatial singular vector associated with the mean spatial frequency used. In one embodiment, for a spatial singular vector with an estimated mean spatial frequency of zero, corresponding to an on-axis signal with no clutter, the weighting is equal to a maximum value of one. As the value of the estimated mean spatial frequency increases, the weighting assigned to the associated spatial singular vector decreases to a minimum of zero. In this way, the high spatial frequency signals containing large amounts of clutter are attenuated, resulting in these signals providing a lower contribution to the final image.

In step 76, the weighted spatial singular vector is used in the construction of the filtered data matrix, $\overline{Y}_{hat}$. The filtered data matrix is described by the following formula.

$$\overline{Y}_{hat} = \Sigma_j \overline{\lambda}_j w(f_j) \overline{U}_j \overline{V}_j^H$$

Where $\overline{\lambda}_j$ is the $j^{th}$ ordered singular value of diagonal matrix $\overline{S}$, $w(f_j)$ is the weighting for the $j^{th}$ right-singular vector, $\overline{U}_j$ is the $j^{th}$ left-singular vector from the data matrix $\overline{Y}$, and $\overline{V}_j^H$ is the conjugate transpose of the $j^{th}$ right-singular vector $\overline{V}_j$. The filtered data matrix can then be used to construct the final clutter-filtered image.

It should be understood that, although the method has been described as employing the use of matrices, other forms of data handling and manipulation may be used in order to achieve off-axis clutter filtering for an ultrasound image. In some instances, the method may be applied to a stream of data being collected by an ultrasound system. Consecutive data points may be used in conjunction with each other or separately.

In summary, embodiments of the invention propose to apply to received echo signal(s) a clutter filter, the filter being based on principles of frequency-based eigenvector filtering.

This principle uses a singular value decomposition (SVD) method applied to e.g. a plurality of echo signals received by a transducer array. The SVD may be performed on a 2D matrix, wherein one dimension of this matrix represents a measured signal at a given transducer array location (a signal of a given transducer channel) and the second dimension corresponds to different measurement samples received for this signal.

The SVD may generate eigenvectors, for instance, wherein the mean spatial frequency distribution and amplitude of these may be used as criteria for filtering.

Embodiments of the invention are based on the fact that presence of the clutter in an ultrasound image manifests in the form of high (mean spatial) frequency eigenvalues and eigenvectors which can be filtered out in said spatial frequency domain. Presence of clutter can also manifest in the amplitude (energy) of the eigenvalues or eigenvectors or their spatial distribution in frequency. A specific clutter filter with a bandpass directed to either of the eigenvalue characteristics, thus, can be implemented.

The invention efficiently rejects off-axis signals from the aligned (i.e. beamformed) ultrasound data, yielding images free of clutter artifacts, enhancing contrast and contributing to better image quality and diagnostic value.

For each pixel, an M*N per-channel data matrix may be estimated from the aligned data received from different observations of that pixel (N=number of channels, M=number of observations). The M observations may be a plurality of time events but also a plurality of transmit directions, directed to the same point of interest. The idea is to obtain different "observations" of a given point.

Further, the SVD decomposition of that matrix may yield the eigenvectors, which correspond to the most important "modes" of the per-channel data. The mean spatial frequency of each eigenvector may be estimated, and the eigenvectors with relatively high mean spatial frequencies (corresponding to off-axis signals) are attenuated prior to reconstruction (reverse reconstruction into the real-space domain).

The filtered per-channel data thus obtained may then be summed to yield a pixel value estimate with attenuated contribution of the off-axis signals.

Embodiments of the present invention may be particularly suitable for tissue imaging.

As discussed above, embodiments make use of a controller for performing the data processing steps.

The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as random-access memory (RAM), programmable read-only memory (PROM), erasable programmable read-only memory (EPROM), and electrically erasable programmable read-only memory (EEPROM). The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for providing a filtered ultrasound image, the method comprising:
   capturing a data matrix using an ultrasonic transducer array, the data matrix containing information relating to an image, wherein elements of each row or column of the data matrix correspond to individual measurements recorded for each of a plurality of ultrasound measurement channels;
   performing singular value decomposition (SVD) on the data matrix;
   obtaining a spatial singular vector from the SVD of the data matrix;
   estimating a mean spatial frequency of the spatial singular vector;
   determining a weighting for the spatial singular vector based on the estimated mean spatial frequency, wherein the weighting is inversely proportional to the mean spatial frequency;
   applying the weighting to the spatial singular vector;
   constructing a filtered data matrix based on the weighted spatial singular vector and the SVD of the data matrix; and
   constructing the filtered ultrasound image, having attenuated contribution from image clutter, based on the filtered data matrix.

2. The method as claimed in claim 1,
   wherein the data matrix comprises N columns,
   wherein N corresponds to a number of ultrasound measurement channels; and
   wherein the data matrix comprises M rows,
   wherein M corresponds to a number of independent measurements recorded for each channel.

3. The method as claimed in claim 2, wherein the M independent measurements are captured from each measurement channel at M points in time during a desired time interval.

4. The method as claimed in claim 1, further comprising forming a covariance matrix based on the data matrix, wherein the SVD is performed on the covariance matrix.

5. The method as claimed in claim 1, wherein the spatial singular vector comprises a spatial eigenvector of the data matrix.

6. The method as claimed in claim 1, wherein the mean spatial frequency is estimated using an autocorrelation technique.

7. The method as claimed in claim 1, wherein the weighting is equal to a maximum of one for the spatial singular vector when the estimated mean spatial frequency is zero, and wherein the weighting decreases to a minimum of zero for the spatial singular vector as the estimated mean spatial frequency increases.

8. The method as claimed in claim 1, wherein the weighting is determined using Gaussian weighting that includes a reference spatial frequency.

9. The method as claimed in claim 1, further comprising discarding a spatial singular vector with a mean spatial frequency above a predetermined value.

10. The method as claimed in claim 1, wherein constructing the filtered data matrix is based on amplitude of the received signal.

11. A controller for providing a filtered ultrasound image in an ultrasound system, wherein the controller is configured to:
capture a data matrix, the data matrix containing information relating to an image, wherein elements of each row or column of the data matrix correspond to individual measurements recorded for each of a plurality of ultrasound measurement channels;
perform singular value decomposition (SVD) on the data matrix;
obtain a spatial singular vector from the SVD of the data matrix;
estimate a mean spatial frequency of the spatial singular vector;
determine a weighting for the spatial singular vector based on the estimated mean spatial frequency, wherein the weighting is inversely proportional to the mean spatial frequency;
apply the weighting to the spatial singular vector;
construct a filtered data matrix based on the weighted spatial singular vector and the SVD of the data matrix; and
construct the filtered ultrasound image, having attenuated contribution from image clutter, based on the filtered data matrix.

12. An ultrasound system comprising:
an ultrasonic transducer array, wherein the ultrasonic transducer array is arranged to emit and receive ultrasonic signals;
a signal processor arranged to compile the received ultrasonic signals into an ultrasound image;
a system for generating a data matrix from the ultrasound image;
a controller as claimed in claim 11; and
an image output device for outputting the filtered ultrasound image.

13. A non-transitory computer-readable medium having stored therein instructions for providing a filtered ultrasound image that, when executed by a processor, cause the processor to:
capture a data matrix, the data matrix containing information relating to an image, wherein elements of each row or column of the data matrix correspond to individual measurements recorded for each of a plurality of ultrasound measurement channels;
perform singular value decomposition (SVD), on the data matrix;
obtain a spatial singular vector from the SVD of the data matrix;
estimate a mean spatial frequency of the spatial singular vector;
determine a weighting for the spatial singular vector based on the estimated mean spatial frequency, wherein the weighting is inversely proportional to the mean spatial frequency;
apply the weighting to the spatial singular vector;
construct a filtered data matrix based on the weighted spatial singular vector and the SVD of the data matrix; and
construct filtered ultrasound image, having attenuated contribution from age clutter, based on the filtered data matrix.

14. The method as claimed in claim 2, wherein the M independent measurements are captured by insonifying a measurement area with M overlapping ultrasonic transmits.

15. The method as claimed in claim 2, wherein the M independent measurements are captured by dividing a physical receive aperture of the ultrasonic transducer array into M overlapping subarrays of size N.

16. The method as claimed in claim 8, wherein the reference spatial frequency corresponds to a transmit beam width.

17. The non-transitory computer-readable medium as claimed in claim 13, the instructions further causing the processor to form a covariance matrix based on the data matrix, wherein the SVD is performed on the covariance matrix.

18. The non-transitory computer-readable medium as claimed in claim 13 wherein the spatial singular vector comprises a spatial eigenvector of the data matrix.

19. The non-transitory computer-readable medium as claimed in claim 13, wherein the mean spatial frequency is estimated using an autocorrelation technique.

20. The non-transitory computer-readable medium as claimed in claim 13, wherein the weighting is determined using Gaussian weighting including a reference spatial frequency.

* * * * *